United States Patent
Koch

(10) Patent No.: US 6,379,389 B1
(45) Date of Patent: Apr. 30, 2002

(54) ARTIFICIAL HIP JOINT SOCKET

(75) Inventor: Rudolf Koch, Oberdorf (CH)

(73) Assignee: Stratec Medical AG, Oberdorf (CH)

( * ) Notice: Subject to any disclaimer, the term of this patent is extended or adjusted under 35 U.S.C. 154(b) by 0 days.

(21) Appl. No.: 09/869,641

(22) PCT Filed: Nov. 3, 1999

(86) PCT No.: PCT/CH99/00514

§ 371 Date: Jul. 2, 2001

§ 102(e) Date: Jul. 2, 2001

(87) PCT Pub. No.: WO01/32108

PCT Pub. Date: May 10, 2001

(51) Int. Cl.$^7$ .................................................. A61F 2/34
(52) U.S. Cl. .................................. 623/22.28; 623/22.15
(58) Field of Search ............................ 623/22.15, 22.28

(56) References Cited

U.S. PATENT DOCUMENTS

| | | | |
|---|---|---|---|
| 3,818,512 A | | 6/1974 | Shersher |
| 3,894,297 A | | 7/1975 | Mittelmeier et al. |
| 4,650,491 A | * | 3/1987 | Parchinski ............... 623/22.28 |
| 5,108,446 A | * | 4/1992 | Wagner et al. ........... 623/22.28 |
| 5,609,645 A | | 3/1997 | Oehy et al. |
| 5,782,928 A | * | 7/1998 | Rires et al. .............. 623/22.21 |
| 5,935,175 A | * | 8/1999 | Ostiguy, Jr. et al. ..... 623/22.22 |

FOREIGN PATENT DOCUMENTS

| | | |
|---|---|---|
| DE | 197 01 778 A | 6/1998 |
| FR | 2 700 686 A | 7/1994 |

* cited by examiner

Primary Examiner—Paul J. Hirsch
(74) Attorney, Agent, or Firm—Rankin, Hill, Porter & Clark LLP

(57) ABSTRACT

A hip-joint socket having an outer shell (1) with a central axis (7) that is to be anchored in the hip bone. The outer shell is detachably mounted, in a geometrically locking manner, on a plastic intermediate shell (1a) exhibiting a hollow-spherical inner side (2). The hip-joint socket also has a wear-resistant inner shell (3) with a spherical outer side (4) and a central axis (8) that is designed to receive a joint ball of a femur shaft. The outer side (4) of the inner shell (3) can be undetachably mounted in a geometrically locking manner to rest against the inner side (2) of the intermediate shell (1a) such that the two central axes (7, 8) coincide. Mutually engaging elements are present at the inner shell and intermediate shell (3 resp. 1a) that consist, on one hand, of a prismatic salient (5) configured at the vertex (9) of the inner shell (10) on the outer side (4) and, on the other hand, of a prismatic recess (6) configured at the vertex (10) of the intermediate shell (1a) on the inner side (2). The salient and recess reliably preclude the mutually contacting inner and intermediate shells (3 resp. 1a) from rotating about their central axes (7, 8) and from canting relative to each other. The salient (5) and the recess (6) are configured in substantially congruent and symmetrical manner relative to the central axes. The hip-joint socket offers minimal design height subjected to optimally distributed resting forces.

11 Claims, 1 Drawing Sheet

ARTIFICIAL HIP JOINT SOCKET

BACKGROUND OF THE INVENTION

1. Field of the Invention

The present invention relates to artificial hip-joint sockets suited for cement-free implantation into the acetabulum.

2. Description of Related Art

Hip-joint sockets adapted for cement-free implantation are known in the art. Such hip-joint sockets have a wear-resistant inner shell comprising a cylindrical salient housing a longitudinally mounted comb, and n intermediate polyethylene shell being fitted with a corresponding recess having an additional elongated slot at its base. The cylindrical salient and the corresponding recess guide the inner and outer shells. The longitudinal comb fitting into the elongated slot secures the two shells against relative rotation. This pre-assembled system may be detachably connected to an outer metal shell during surgery. This connection is implemented using a deforming polyethylene detent device. The titanium or titanium-alloy outer shell is connected to the bone without resort to cementing.

This known hip-joint socket incurs the drawback of a substantial height of the wear-resistant inner shell caused by the superposition of the guide elements and the rotationally locking elements. Another drawback is that the longitudinal comb of the inner shell applies, on account of its geometry, concentrated stresses at the inner side of the elongated slot of the intermediate shell. As a consequence ceramic materials, which disadvantageously react to such stresses, cannot be used.

SUMMARY OF THE INVENTION

The present invention is directed toward an artificial hip-joint socket implementing optimal spreading of the applied forces at minimal design height.

The design of the invention offers the advantage that the prismatic elements at the inner and intermediate shells simultaneously guide the shells and also secure them against rotation and canting. The inventive design, as a result, has a reduced height. This reduced height, on the one hand, permits smaller sockets and lesser wall thickness of the intermediate shell, while, on the other hand, even very small sockets allow congruence of the radius insertion point relating to inner slide surface and outer geometry. This feature amounts to kinematically optimal hip-joint reconstruction.

Compared with the state of the art, the present invention offers improved, omnidirectionally more uniformly distributed canting and rotational forces between the inner and the intermediate shells. In other words, torques exerted by the joint's ball on the inner shell are optimally transferred by means of the intermediate and the outer shells to the hip bone.

In a preferred embodiment, the salient of the inner shell and the corresponding recess in the intermediate shell each substantially represent a regular tetragonal prism. In this manner, the applied forces are spread or distributed optimally. The length of the regular sides of the tetragonal prism may be in the range of 10 to 18 mm, preferably 13 to 15 mm.

The elevation of the prismatic salient and that of the prismatic recess is in the range of 2 to 6 mm, preferably 3.5 to 4.5 mm. The facets implemented by rounding or cutting further reduce the wall thickness at the intermediate shell and this feature enables system integration into small outer shells and, hence, also into small acetabuli.

The overall height of the inner shell, inclusive the salient, shall be at most 65%, preferably at most 60% of the maximum diameter of the inner shell (3).

Preferably the wear-resistant inner shell is composed of a CoCr alloy or of a ceramic such as $Al_2O_3$.

BRIEF DESCRIPTION OF THE DRAWINGS

These and further features of the invention will be apparent with reference to the following description and drawings, wherein.

DETAILED DESCRIPTION OF THE PREFERRED EMBODIMENT

Figure 2:
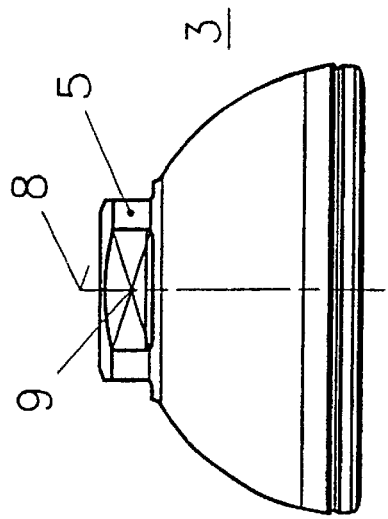
FIG. 2 is a side elevational view of the inner shell of FIG. 1.
Figure 3:
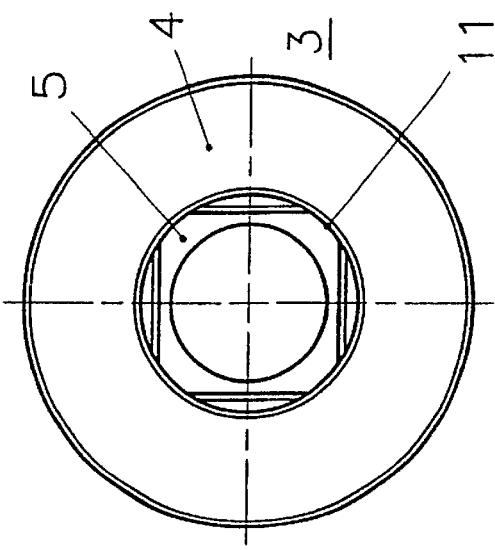
FIG. 3 is a top plan view of the inner shell of FIG. 1.

The artificial hip-joint socket shown in FIGS. 1 through 4 comprises, on one hand, a titanium outer shell 1 with a central axis 7 and intended to be anchored in the hip bone. The outer shell 1 is detachably joined in geometrically locking manner to a plastic intermediate shell 1a having a hollow spherical inside surface 2. The artificial hip-joint socket, on the other hand, comprises a wear-resistant inner shell 3 made of an aluminum oxide ceramic and comprising a spherical outer side 4 and a central axis 8 and intended to receive a swivel of a femur shaft.

The outer side 4 of the inner shell 3 can be permanently affixed to rest in a geometrically locking manner against the inner side 2 of the intermediate shell 1a. Consequently, the central axis 7 of the outer shell 1 coincides with the central axis 8 of the inner shell 3.

Figure 1:
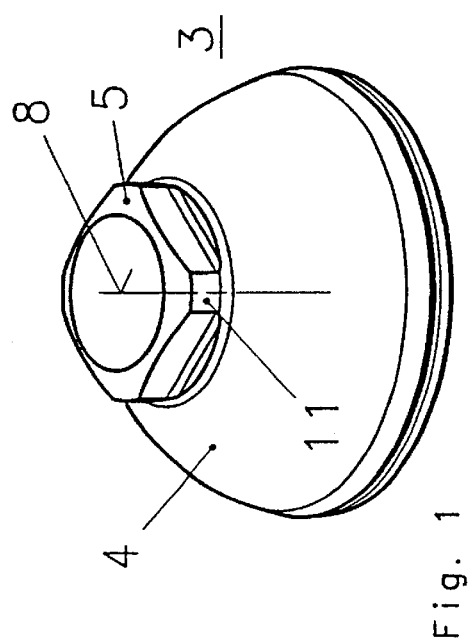
FIG. 1 is a perspective of the inner shell of the hip-joint socket according to the present invention.
Figure 4:
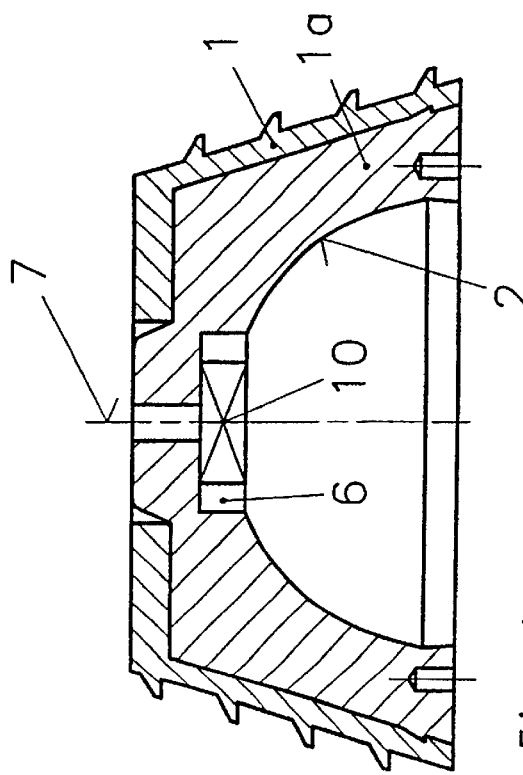
FIG. 4 is a cross-sectional view of the outer shell and intermediate shell of the hip-joint socket according to the present invention.

Mutually engaging elements are present at the inner and intermediate shells 3 and 1a to secure the inner and intermediate shells 3 and 1a against rotation about their central axes 7 and 8 and against canting relative to each other once they rest against each other. These anti-rotation and anti-canting elements consist on one hand of a prismatic salient 5 mounted at the vertex 9 of the inner shell 3 on the outer side 4, and, on the other hand, of a prismatic recess 6 configured on a vertex 10 of the intermediate shell 1a at the inner side 2. The salient 5 and the recess 6 are substantially congruent and also symmetric to the central axes 7 and 8 and each represent a regular, tetragonal prism. The regular sides of the tetragonal prism are 14 mm long; however, they are cut off by a length of 1.2 mm and, in this manner, they subtend four facets 11 (FIG. 1).

The heights or elevations of the prismatic salient 5 and of the prismatic recess 6 each amount to 4 mm. The total height or elevation of the inner shell 3, including the salient 5, is 55% of the maximum diameter of the inner shell 3.

The individual steps in implanting the artificial hip-joint socket of the invention will now be described:

(1) conical or spherical milling of the acetabulum, (2) inserting the cementless, titanium outer shell 1 to be anchored (spherically by a pressfit and conically by means of a threaded socket) in the acetabulum prepared in the manner of step (1), (3) where called for, placing bone screws through appropriate holes in the modular titanium outer shell 1, (4.1) knocking the sandwich inlay—which consists of the plastic intermediate shell 1a and the wear-resistant inner shell 3—into the outer shell 1, (4.2) the plastic intermediate shell 1a is connected to the outer shell 1 by a conventional polyethylene detent element (not shown), (4.3) the wear resistant inner shell 3 is anchored on the plastic intermediate shell 1a by means of the prismatic salient 5 of the invention and the matching prismatic recess 6 of the invention and by means of a conventional detent lock or a mating cone, (5) repositioning the hip joint while detenting the joint ball into the artificial hip socket.

The present invention has been described herein with particularity, but it is noted that the scope of the invention is not limited thereto. Rather, the present invention is considered to be possible of numerous modifications, alterations, and combinations of parts and, therefore, is only defined by the claims appended hereto.

What is claimed is:

1. An artificial hip-joint socket comprising:

(a) an outer shell (1) comprising a central axis (7) to be anchored into the hip bone and which can be detachably affixed in a geometrically locking manner to a plastic intermediate shell (1a) comprising a hollow-spherical inside surface (2), (b) a wear-resistant inner shell (3) comprising a spherical outer side (4) and a central axis (8) designed to receive a joint ball of a femur shaft, wherein (c) the outer side (4) of the inner shell (3) can be made to undetachably rest in a geometrically locking manner on the inner side (2) of the intermediate shell (1a) such that the two central axes (7, 8) coincide, and (d) mutually engaging elements are present at the inner and outer shells (3 and 1a resp.) which secure the mutually contacting inner and intermediate shells (3 and 1a resp.) against rotation about their central axes (7 and 8) and against mutual canting, wherein: the elements precluding rotation and canting consist of (e) a prismatic salient (5) configured at a vertex (9) of the inner shell (3) on the outer side (4), and (f) a prismatic recess (6) configured at a vertex (10) of the intermediate shell (1a) on the inner side (2), where (g) the salient (5) and the recess (6) are configured in substantially congruent manner, (h) the salient (5) and the recess (6) are configured substantially symmetrically to the central axes (7 resp. 8), and (i) the elevation of the prismatic salient (5) and the elevation of the prismatic recess (6) are each between about 2 to 6 mm.

2. The hip-joint socket as claimed in claim 1, wherein the salient (5) and the recess (6) each substantially represent a regular tetragonal prism.

3. The hip-joint socket as claimed in claim 2, wherein a length of regular sides of the tetragonal prism is between about 10 to 18 mm.

4. The hip-joint socket as claimed in claim 1, wherein at least the prismatic longitudinal edges (11) of the salient (5) are rounded or cut off.

5. The hip-joint socket as claimed in claim 4, wherein the longitudinal edges are cut off by a length of 0.8 to 1.5 mm.

6. The hip-joint socket as claimed in claim 1, wherein a height of the prismatic salient (5) and that of the prismatic recess (6) are each between about 3.5 to 4.5 mm.

7. The hip-joint socket as claimed in claim 1, wherein a total height of the inner shell (3), including the salient (5), amounts to at most 65% of the maximum diameter of the inner shell (3).

8. The hip-joint socket as claimed in claim 7, wherein the total height of the inner shell (3), inclusive the salient (5), at most amounts to 60% of the maximum diameter of the inner shell (3).

9. The hip-joint socket as claimed in claim 1, wherein the wear-resistant inner shell (3) is made of a material selected from the group consisting of a CoCr alloy or a ceramics.

10. The hip-joint socket as claimed in claim 1, wherein the wear-resistant inner shell (3) is made of $Al_2O_3$.

11. The hip-joint socket as claimed in claim 2, wherein a length of regular sides of the tetragonal prism is between about 13 to 15 mm.

\* \* \* \* \*

UNITED STATES PATENT AND TRADEMARK OFFICE
CERTIFICATE OF CORRECTION

PATENT NO. : 6,379,389 B1
DATED : April 30, 2002
INVENTOR(S) : Kock

It is certified that error appears in the above-identified patent and that said Letters Patent is hereby corrected as shown below:

<u>Title page,</u>
Item [56], References Cited, U.S. PATENT DOCUMENTS, delete "5,609,645" and insert -- 5,609,648 --.

Signed and Sealed this

Twenty-fourth Day of September, 2002

Attest:

JAMES E. ROGAN
Attesting Officer    Director of the United States Patent and Trademark Office